United States Patent [19]

Doerges et al.

[11] 4,318,716
[45] Mar. 9, 1982

[54] PROCESS OF REGENERATING LADEN ABSORBENTS

[75] Inventors: Alexander Doerges; Manfred Kriebel, both of Frankfurt; Johann Schlauer, Frankfurt-Goldstein, all of Fed. Rep. of Germany

[73] Assignee: Metallgesellschaft, Aktiengesellschaft, Frankfurt, Fed. Rep. of Germany

[21] Appl. No.: 170,414

[22] Filed: Jul. 21, 1980

Related U.S. Application Data

[63] Continuation of Ser. No. 82,495, Oct. 9, 1979, abandoned, which is a continuation of Ser. No. 856,058, Nov. 30, 1977, abandoned.

[30] Foreign Application Priority Data

Dec. 2, 1976 [DE] Fed. Rep. of Germany ....... 2654579

[51] Int. Cl.³ .................. B01D 19/00; B01D 53/14
[52] U.S. Cl. .................................... 55/48; 55/51; 55/89; 210/634; 423/229
[58] Field of Search ............ 55/44, 48, 51, 73, 89; 210/634; 423/229

[56] References Cited

U.S. PATENT DOCUMENTS

| | | | |
|---|---|---|---|
| 2,791,290 | 5/1957 | Natta | 55/44 |
| 3,324,627 | 6/1967 | Kohrt | 55/51 X |
| 3,505,784 | 4/1970 | Hochgesand et al. | 55/44 |
| 3,653,809 | 4/1972 | Wehner et al. | 55/73 X |
| 3,739,548 | 6/1973 | Hegwer | 55/48 X |
| 3,880,615 | 4/1975 | Grunewald et al. | 55/44 |
| 3,918,934 | 11/1975 | Kriebel et al. | 55/48 |
| 4,011,066 | 3/1977 | Bratzler et al. | 55/44 |

*Primary Examiner*—Robert H. Spitzer
*Attorney, Agent, or Firm*—Sprung, Felfe, Horn, Lynch & Kramer

[57] ABSTRACT

An improvement in a process of regenerating a hydrocarbon laden water miscible high boiling organic solvent obtained by scrubbing a hydrocarbon-containing gas with said water miscible high boiling organic solvent at normal temperature and super atmospheric pressure, wherein the laden solvent is regenerated by flashing, heating and/or stripping, cooled and recycled to the scrubbing step, the improvement comprising:

A. adding liquid hydrocarbons to at least a part of said regenerated solvent and thereafter extracting the resultant mixture in the presence of water whereby to obtain a hydrocarbon rich phase and an aqueous phase containing said solvent;

B. separating said aqueous phase from said hydrocarbon rich phase and recycling said aqueous phase to the regeneration step; and C. withdrawing said hydrocarbon rich phase.

12 Claims, 1 Drawing Figure

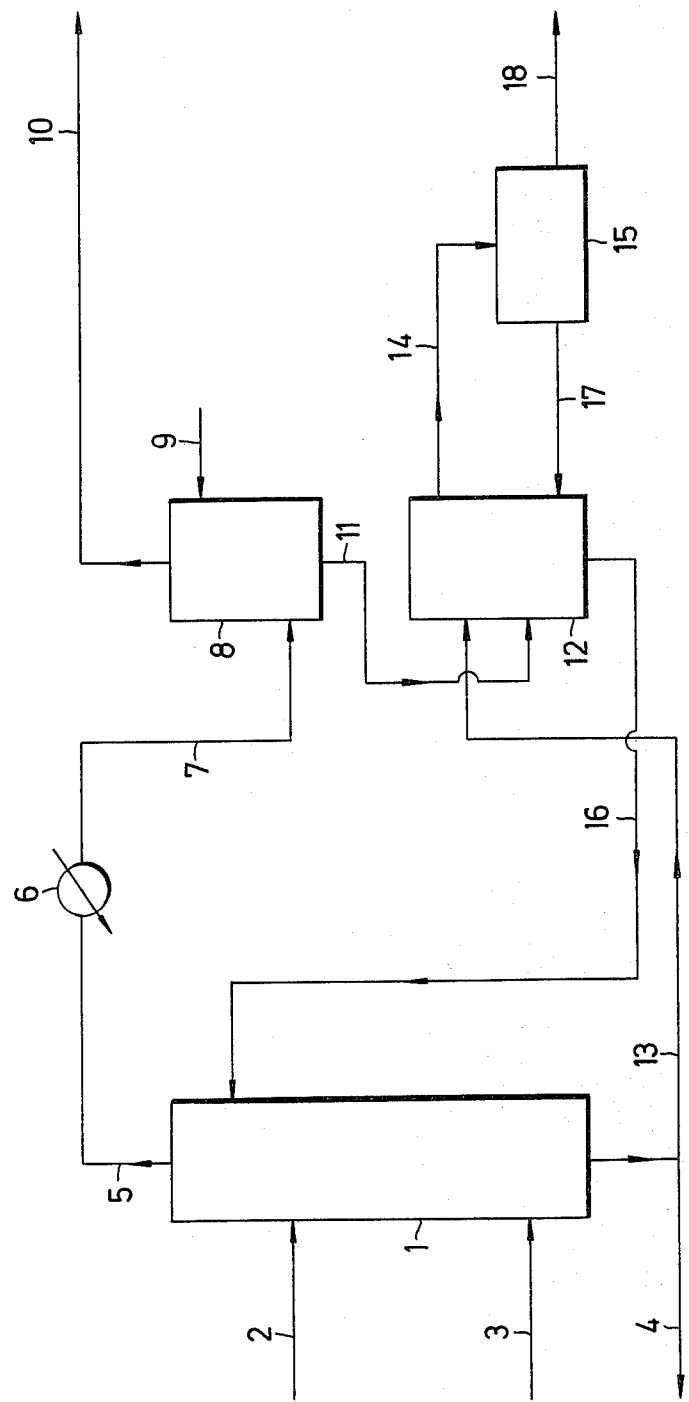

PROCESS OF REGENERATING LADEN ABSORBENTS

This is a continuation of application Ser. No. 082,495, filed Oct. 9, 1979, which, in turn, is a continuation of application Ser. No. 856,058, filed Nov. 30, 1977, (both now abandoned).

BACKGROUND OF THE INVENTION

1. Field of the Invention

This invention relates to the regeneration of solvents, laden with hydrocarbons. More especially this invention relates to the regeneration of hydrocarbon-containing high boiling organic solvents which are miscible with water wherein the laden solvent is regenerated by flashing, heating and/or stripping. This invention is particularly concerned with the regeneration of such hydrocarbon-containing water miscible high boiling organic solvents in a process whereby the hydrocarbons can be separately removed.

2. Discussion of the Prior Art

It is known to desulfurize gases at normal temperature and elevated pressure by scrubbing the gases in a plurality of stages with a high-boiling, water-soluble organic liquid. The laden absorbent is regenerated by being flashed and stripped at elevated temperatures.

Part of the regenerated solvent is extracted with water to remove water in soluble constituents. The water insoluble components are separated and the absorbent which has been diluted with water is returned to the main cycle (U.S. Pat. No. 4,011,066).

The known process is restricted to the purification of gases which have been produced by a gasification of solid fossil fuels by a treatment with steam and oxygen under superatmospheric pressure.

On the other hand, the solubility of higher boiling hydrocarbons in the organic solvents which are employed is much higher than that of acid gas constituents. For this reason, such hydrocarbons are removed only in part by the regeneration and become enriched in the solvent.

The extraction of the regenerated solvent with water in the known process is not sufficient for a complete removal of the high boiling hydrocarbons although such removal is required for certain gases if trouble in operation is to be avoided.

It is an object of the invention to avoid these disadvantages and to propose a process which may be used also to purify natural gases.

The higher boiling hydrocarbons still contained in the regenerated solvent should be removed as completely as possible.

SUMMARY OF THE INVENTION

In accordance with this invention the objects of avoiding the disadvantages attendant the prior art processes are obtained by an improved process for regenerating a hydrocarbon laden water miscible high boiling organic solvent obtained by scrubbing a hydrocarbon-containing gas with said water miscible high boiling organic solvent at a normal temperature and superatmospheric pressure wherein the laden solvent is regenerated by flashing, heating and/or stripping, cooled and recycled to the scrubbing step. The improvement in accordance with the invention comprises:

A. adding liquid hydrocarbons to at least a part of said regenerated solvent and thereafter extracting the resulting mixture in the presence of water whereby to obtain a hydrocarbon rich phase and an aqueous phase containing said solvent;

B. separating said aqueous phase from said hydrocarbon rich phase and recycling said aqueous phase to the regeneration step; and C. withdrawing said hydrocarbon rich phase. The hydrocarbon rich phase can then be recovered.

The objects of the overall process are accomplished by a series of steps as follows:

1. Initially the gases are scrubbed with the water miscible high boiling organic solvent whereby the solvent becomes hydrocarbon laden.
2. The laden solvent is regenerated by flashing, heating and/or stripping.
3. The so regenerated solvent is treated by having liquid hydrocarbons added thereto and extraction effected in the presence of water whereby there is formed a hydrocarbon rich phase and an aqueous phase containing the solvent.
4. The phases which form permit separation of the aqueous phase containing the solvent from the hydrocarbon rich phase.
5. The aqueous phase containing the solvent is recycled to the regeneration step.
6. The hydrocarbon rich phase is withdrawn. Preferably, the liquid hydrocarbons which are added contain at least 10% by weight aromatic hydrocarbons. Generally, the hydrocarbons are C 3 to C 22 hydrocarbons and they are preferably added in a quantity of 3 to 30% by volume based upon the volume of the regenerated water miscible organic solvent.

The extraction is generally effected in an extraction vessel or a series of vessels as explained below. Generally the regenerated solvent is removed from a regeneration column and passed through one or more extraction vessels to which the hydrocarbons and water are added. The water content is preferably maintained at at least 30% and preferably 50 to 100% by volume of the regenerated absorbent.

According to another and preferred feature of the invention the regenerated absorbent is subjected to countercurrent extraction, all or part of the water used for the extraction suitably recovered from the regeneration of the separated aqueous phase which has been separated by the extraction and fed to the top of the regenerating column.

It is within the scope of the invention to cool the mixed gases and vapors which become available as a result of the stripping step, to condense them and to feed the resulting condensate, which contains hydrocarbons, solvent and water, to the extracting step.

It has been found to be desirable to maintain a temperature of 20° to 70° C. during the extracting and/or separating steps and to effect the separation with a residence time of at least 10 minutes and preferably 30 to 90 minutes.

In accordance with a preferred feature of the invention, the organic solvent which is employed consists of an N-alkylated lactam, preferably N-methyl pyrrolidone.

In accordance with a preferred feature of the invention, a soluble organic amine is added to the regenerated absorbent in an amount of 0.2 to 5 grams per liter, before the extraction. That amine may consist of one or more alkanolamines, preferably diethanolamine or diisopropanolamine.

The advantages afforded by the invention reside particularly in that the improved process can be used to purify at superatmospheric pressure virtually all gases which have been commercially produced by a gasification and natural gases in a simple manner. The organic solvent which is laden with the impurities that have been scrubbed off can be completely regenerated in accordance with the invention so that trouble in operation, e.g., as a result of deposits or foaming, are avoided.

Within the scope of the invention, the products which become available in operation are used so that extraneous substances are not required. For this reason the process is highly economical.

BRIEF DESCRIPTION OF DRAWING

The invention can be more readily understood and appreciated when reference is made to the accompanying drawing which diagrammatically shows a plant for carrying out the process of the invention.

DESCRIPTION OF SPECIFIC EMBODIMENT

Referring to the drawing, a regenerating column 1 is associated with the scrubbing process. The circulated solvent is heated and is fed through conduit 2 into the upper portion of the regenerating column 1 and flows therein in countercurrent to a stripping gas 3 so that dissolved acid gas constituents and volatile hydrocarbons are removed from the solvent, which is then recycled to the scrubber through conduit 4. The hot overhead gases leave the regenerating column 1 through conduit 5.

Those components of the overhead gas which are condensible at the cooling water temperature in the condenser 6 are condensed in the latter and the overhead gas is then fed through a conduit 7 into a rescrubbing column 8. The latter is fed through conduit 9 with water, which flows in countercurrent to the overhead gas to remove residual solvent vapor therefrom.

The overhead gas is withdrawn from the process via conduit 10. The liquid sump product of the re-scrubbing column 8 consists of solvent, hydrocarbons and water and is fed through conduit 11 to an extractor 12 for a separating step.

The extractor 12 is fed at the same time through conduit 13 with a solvent partial stream, in which the hydrocarbons which have not been removed in regenerating column 1 are dissolved. In the extractor 12, a separation of layers results in the formation of a light phase rich in hydrocarbons and a heavy phase, which consists mainly of solvent and water.

The hydrocarbon phase can be transferred from the upper portion of extractor 12 through conduit 14 into condenser 15 and be collected therein. The solvent-water heavy phase is withdrawn from the lower portion of the extractor 12 and is fed through conduit 16 to the top of the regenerating column 1 to strip the water from the solvent with the rising gases.

To control the required hydrocarbon concentration, particularly the content of aromatics, a hydrocarbon partial stream can be recycled from the container 15 through conduit 17 into the extractor 12. The separated hydrocarbons which have been collected in the container 15 are withdrawn from the process by conduit 18.

In order to more fully illustrate the nature of the invention and the manner of practicing the same the following example is presented.

EXAMPLE

In the plant shown on the drawing, natural gas at a rate of 200,000 standard $m^3/h$ are desulfurized by being scrubbed under a pressure of 75 bar with a solvent consisting of N-methyl pyrrolidone at a rate of 165 $m^3/h$. The solvent is recirculated for re-use in scrubbing the gas. The laden solvent is first passed through a plurality of flashing stages and is then heated and fed through conduit 2 to the upper portion of the regenerating column 1, which is fed through conduit 3 with stripping gas at a rate of 5000 standard $m^3/h$ to remove the sulfur components as well as the absorbed volatile hydrocarbons to a residual content of up to 2% by volume in the boiling range of 200° C. and higher.

The re-scrubbing column 8 is fed via 7 with hot condensed gases from cooler 6 and with re-scrubbing water from conduit 9. Sump product is collected in the re-scrubbing column 8 at a rate of 1884 kg/h and is composed of 13.0% by weight solvent, 79.9% by weight water and 7.1% by weight (=134 kg/h) hydrocarbons. The sump product is fed through conduit 11 to the extractor 12.

The upper portion of the extractor 12 is fed through conduit 13 with a partial stream of regenerated solvent at a rate of 3000 kg/h. That solvent contains up to 2% by volume hydrocarbons. Hydrocarbons which contain aromatics are simultaneously returned from the container 15 through conduit 17 at a rate of 700 kg/h.

When separation has been effected, hydrocarbons at a rate of 884 kg/h can be withdrawn from extractor 12 through conduit 14 into the container 15. Hydrocarbons at a rate of 184 kg/h are withdrawn from the process, specifically from the container 15, through conduit 18.

The solvent-water heavy phase which has been separated becomes available at a rate of 4700 kg/h and is withdrawn from the extractor 12 through conduit 16 and is fed as reflux to the regenerating column 1. The disturbing heavy hydrocarbons which have become available at a rate of 50 kg/h are no longer contained in that phase but are withdrawn from the process through conduit 18 together with the other lighter hydrocarbons from the sump of the re-scrubbing column 8.

Within the scope of the invention, the process can be carried out in a simpler mode in that the components are fed to the extractor 12 in a different sequence and/or in different proportions or the extractor 12 is replaced by a mixer and a simple separating vessel. The extraction or the simple separation should desirably be effected at a temperature of 20° to 70° C. because the separation can be accomplished most economically in that temperature range. If the countercurrent extractor 12 is replaced by a mixer and a simple separating vessel, the separating space must be so large that the residence time of the mixture is at least 10 minutes, preferably 30 to 90 minutes, so that the high-boiling hydrocarbons are sufficiently separated from the solvent.

What we claim is:

1. A process for regenerating a hydrocarbon laden water miscible high boiling organic solvent obtained by scrubbing a hydrocarbon containing gas with said water miscible high boiling organic solvent at normal temperature and superatmospheric pressure which comprises
   A. Stripping said hydrocarbon laden water miscible high boiling organic solvent whereby to obtain a mixture of volatile hydrocarbons containing gases and vapors and leave behind regenerated liquid solvent comprising said high boiling organic solvent and hydrocarbons;

B. Condensing said gases and vapors whereby to obtain a condensate containing hydrocarbons and water;

C. Contacting a partial stream of said regenerated solvent with said volatile hydrocarbon in a quantity of 3 to 30% by volume of the regenerated solvent to obtain a hydrocarbon rich phase and an aqueous phase containing said solvent wherein the water content is maintained at at least 30% by volume of the regenerated solvent;

D. Separating said aqueous phase from said hydrocarbon rich phase and recycling said aqueous phase to said regeneration; and E. Withdrawing at least a portion of said residual hydrocarbon rich phase.

2. A process according to claim 1 wherein the liquid hydrocarbons in the condensate of steps B and C contain at least 10% by weight aromatic compounds.

3. A process according to claim 2 wherein the water content is maintained at 50 to 100% by volume of the regenerated solvent.

4. A process according to claim 1 wherein the regenerated solvent is subjected to a countercurrent extraction in step C.

5. A process according to claim 1 wherein step C and/or the separation of step D are performed at a temperature of 20° to 70° C.

6. A process according to claim 1 wherein the separation of step D is effected over a period of time of at least 10 minutes.

7. A process according to claim 6 wherein said separation is effected over a period of time of 30 to 90 minutes.

8. A process according to claim 1 wherein the organic solvent is N-alkylated lactam.

9. A process according to claim 8 wherein said N-alkylated lactam is N-methyl pyrrolidone.

10. A process according to claim 1 wherein a soluble organic amine is added to the regenerated solvent in an amount of 0.2 to 5 g/l before the extraction of step C.

11. A process according to claim 10 wherein said soluble organic amine is one or more alkanolamines.

12. A process according to claim 11 wherein said alkanolamine is diethanolamine or diisopropanolamine.

* * * * *